United States Patent [19]

Schroeder et al.

[11] Patent Number: 5,015,578

[45] Date of Patent: May 14, 1991

[54] BMY-41950 ANTITUMOR ANTIBIOTIC

[75] Inventors: Daniel Schroeder, Higganum; Kin S. Lam, Cheshire; Jacqueline Mattei, East Haven; Grace A. Hesler, Branford, all of Conn.

[73] Assignee: Bristol-Myers Squibb Company, New York, N.Y.

[21] Appl. No.: 482,364

[22] Filed: Feb. 20, 1990

Related U.S. Application Data

[63] Continuation-in-part of Ser. No. 327,929, Mar. 23, 1989, abandoned.

[51] Int. Cl.$^5$ ............... C12P 17/00; C12P 19/00; C12N 1/20; C07H 19/00
[52] U.S. Cl. ..................... 435/119; 435/85; 435/169; 435/75; 435/253.5; 435/898; 540/545; 536/22
[58] Field of Search ............. 435/119, 169, 85, 75, 435/253.5, 898; 536/22; 540/545, 543

[56] References Cited

U.S. PATENT DOCUMENTS

| | | | |
|---|---|---|---|
| 4,107,297 | 8/1978 | Omura et al. | 435/169 |
| 4,390,546 | 6/1983 | Goetz et al. | 514/450 |
| 4,923,986 | 5/1990 | Murakata et al. | 540/545 |

Primary Examiner—Johnnie R. Brown
Assistant Examiner—Pamela S. Webber
Attorney, Agent, or Firm—David M. Morse

[57] ABSTRACT

A new antitumor antibiotic designated BMY-41950 is produced by fermentation of *Streptomyces staurosporeus* ATCC 55006 or *Streptomyces hygroscopicus* ATCC 53730. The BMY-41950 antibiotic exhibits both antimicrobial and antitumor activities.

3 Claims, No Drawings

BMY-41950 ANTITUMOR ANTIBIOTIC

CROSS-REFERENCE TO RELATED APPLICATION

This application is a continuation-in-part of our co-pending application Serial No. 327,929 filed on Mar. 23, 1989.

BACKGROUND OF THE INVENTION

1. Field of the Invention

This invention relates to a novel antitumor antibiotic and to its production and recovery.

2. Description of the Prior Art

U.S. Pat. No. 4,107,297 discloses production of an antibiotic AM-2282 by fermentation of *Streptomyces staurosporeus* nov. sp. ATCC 55006. This antibiotic reportedly has antiinfective and hypotensive activity. AM-2282 was later named staurosporine and its structure is reported in *J. Chem. Soc. Chem. Commun.* 1978: 800–801, 1978 to be

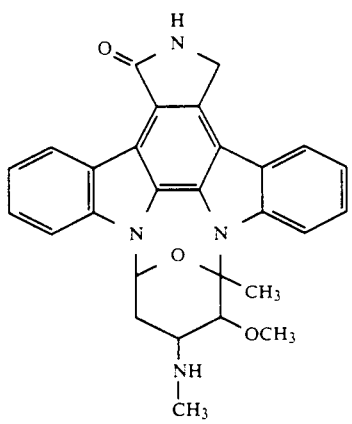

European Published Patent Application 238,011 discloses an antitumor antibiotic named UCN-01 produced by fermentation of *Streptomyces* sp. UCN-01 (FERM BP-990) having the structure

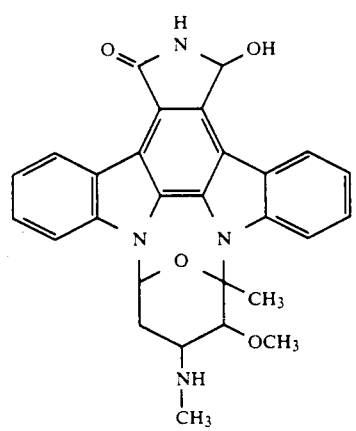

compound UCN-01 is also described in *J. Antibiotics*, p. 1782, December 1987.

The antitumor antibiotic named rebeccamycin is disclosed in U.S. Pat. No. 4,552,842 as being produced by fermentation of *Nocardia aerocolonigenes* ATCC 39243. Rebeccamycin has the structural formula

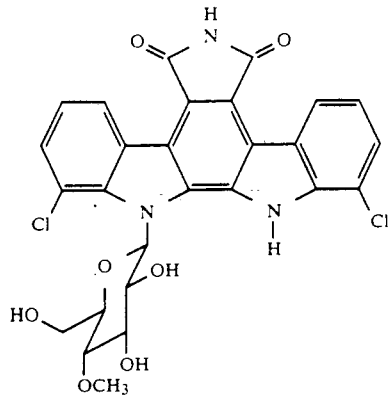

The producing organism has recently been reclassified as *Saccharothrix aerocolonigenes* (*J. Antibiot.* 40: 668–678, 1987).

U.S. Pat. No. 4,524,145 discloses the antitumor antibiotic named 4'-deschlororebeccamycin which is produced by fermentation of *Saccharothrix aerocolonigenes* ATCC 39243. This compound has the structural formula

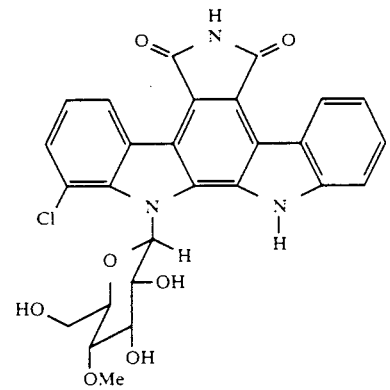

U.S. patent application Ser. No. 933,428 filed Nov. 21, 1986 discloses a series of antitumor antibiotics of the formula

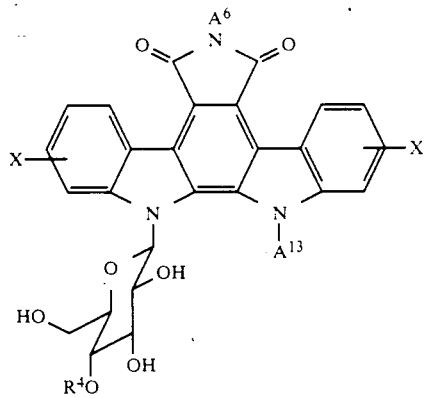

wherein:

n is an integer from 1 to 6;

$A^6$ and $A^{13}$ are selected from H and $-(CH_2)NR^1R^2$ of $A^6$ and $A^{13}$ is $-(CH_2)_n-NR^1R^2$;

$R^1$ and $R^2$, independently are selected from hydrogen unsubstituted and substituted $C_1-C_6$ alkyl, aralkyl having 1 to 3 carbons in the alkyl moiety and unsubstituted phenyl or phenyl substituted with 1 to 3 alkyl, alkoxy hydroxy, halo, carboxyl, alkoxycarbonyl, and amino and mono- and di-lower-alkylamino groups in the aryl moiety, and aryl selected from unsubstituted phenyl and phenyl substituted with 1 to 3 alkyl, alkoxy, hydroxy, halo, amino, mono- and dialkylamino, nitro, carboxyl, alkoxycarbonyl, and cyano groups provided that both $R^1$ and $R^2$ are not each aryl and, when taken together, $R^1$ and $R^2$ may be selected from $-(CH_2)_4-$ and $(CH_2)_2-R^3-(CH_2)_2-$ to form a 5- or 6-membered ring together with the N-atom wherein $R^3$ is selected from $CH_2$, NH, O and S;

X is selected from H, F, Cl, Br, $C_1-C_3$ alkyl, OH, carboxyl, alkoxycarbonyl and alkoxy wherein the alkyl moiety is $C_1-C_3$ alkyl, benzyloxy, amino, and mono- and dialkylamino; and $R^4$ is selected from H and $CH_3$; and pharmaceutically acceptable acid addition and base salts thereof.

European Published Patent Application 175,284 discloses four antitumor antibiotics designated AT2433A1, AT2433A2, AT2433B1 and AT2433B2 produced by fermentation of *Actinomadura melliaura* ATCC 39691. These compounds have the structural formulae

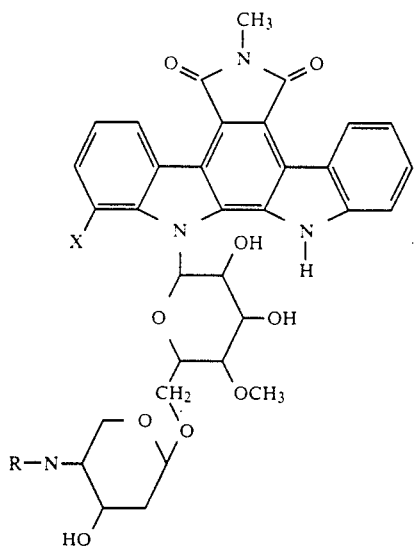

wherein X is H or Cl and R is H or $CH_3$.

PCT Application W088/07045 discloses derivatives of the compound K252 which are reported to have in vitro antitumor activity against certain cell lines. Among the compounds disclosed are certain 7-oxo derivatives of K252 which appear as compounds 65-76 on page 44.

SUMMARY OF THE INVENTION

This invention relates to a new antitumor antibiotic designated herein as BMY-41950 having the structural formula

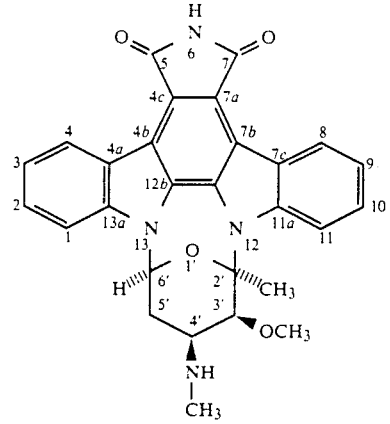

and to the process for the preparation, isolation and purification of BMY-41950 in substantially pure form.

Antibiotic BMY-41950 may be obtained by fermentation of a BMY-41950-producing strain of *Streptomyces staurosporeus* nov. sp., preferably *Streptomyces staurosporeus* ATCC 55006 or a mutant or variant thereof, or a BMY-41950-producing strain of *Streptomyces hygroscopicus*, preferably *Streptomyces hygroscopicus* strain C39280-450-9 (ATCC 53730) or a mutant or variant thereof, in an aqueous nutrient medium under submerged aerobic conditions until a substantial amount of BMY-41950 is produced by said microorganism in said culture medium and recovering the BMY-41950 from the culture medium substantially free of co-produced substances.

BMY-41950 exhibits antimicrobial activity and also activity against experimental animal tumor systems.

DETAILED DESCRIPTION

The BMY-41950 antibiotic of the present invention may be produced by fermentation of a BMY-41950-producing strain of *Streptomyces staurosporeus* or *Streptomyces hygroscopicus*.

An especially preferred BMY-41950-producing strain has been obtained from the Northern Regional Research Center. U.S. Department of Agriculture, ARS Patent Culture Collection, where it is identified as NRRL 11,184 *Streptomyces* sp. A biologicall pure culture of strain NRRL 11,184 has been deposited with the American Type Culture Collection. Rockville, Md. and added to their permanent collection of microorganisms as ATCC 55006. Cultures of this strain are also maintained as lyophiles in the Bristol-Myers Squibb Company PRDD Actinomycete Culture Collection, Wallingford, Ct.

Taxonomic studies on NRRL 11,184 have been described in detail in U.S. Pat. No. 4,107,297 and in *J. Antibiotics* 30(4):272-282, 1977. The strain has been classified as a new *Streptomyces* species with the name *Streptomyces staurosporeus* nov. sp.

Another especially preferred BMY-41950-producing organism is a novel strain of *Streptomyces hygroscopicus* designated herein as *Streptomyces hygroscopicus* strain C39280-450-9. This strain was isolated from a soil sample collected at Numazu prefecture, Japan. A biologically pure culture of strain C39280-450-9 has been deposited with the American Type Culture Collection, Rockville, Md. and added to their permanent collection of microorganisms as ATCC 53730. This culture, designated as C39280, is also maintained as a dormant culture in lyophile tubes and cryogenic vials in the Bristol-Myers Squibb Pharmaceutical Research and Development Division Culture Collection, Wallingford, Ct.

The results of taxonomic studies performed on strain C39280-450-9 indicate that the strain is a novel strain of *Streptomyces hygroscopicus*. Strain C39280-450-9 has the following properties as determined by materials and procedures described by Shirling & Gottlieb (Int. J. Sept. Bacteriology 16: 313–340, 1966; ibid. 18: 69–189. 1968; ibid. 22: 265–394, 1972). Staneck & Roberts (Appl. Microbiol. 28: 226–31, 1974). K. P. Schaal (M. Goodfellow and D. E. Minnikin Eds., Chemical Methods in Bacterial Systematics, Academic Press Inc. pp. 359–381, 1985).

MORPHOLOGY

Morphological characteristics of strain C39280-450-9 include: (1) the formation of non-fragmenting substrate and aerial mycelia (2) spiral chains of arthrospores borne from branched sporophores on the aerial mycelium, the spore chains having 2 to 6 turns, (3) smooth spore ornamentation.

CULTURAL AND PHYSIOLOGICAL CHARACTERISTICS

Cultural characteristics as observed on descriptive media are summarized in Table 1. Hygroscopic change is evident in ISP medium no. 4 and Modified Bennett's medium. Soluble potato starch and glucose are utilized for growth. Utilization of inositol is questionable. Physiological characteristics are summarized in Table 2.

CELL WALL CHEMISTRY

Analysis of strain C39280-450-9 whole cell hydrolysates revealed LL-diaminopimelic acid, galactose, ribose, and mannose as cell wall components, hence the organism's Type I cell wall assignment. Phospholipid analysis detected the presence of phosphatidyl ethanolamine and phosphatidyl glycerol, typing the phospholipid pattern as PII.

TABLE 1

Cultural Characteristic of Strain C39280-450-9

| Agar medium | Growth | Reverse color | Aerial mycelium | Pigment |
|---|---|---|---|---|
| ISP 2 | moderate | colorless | moderate | oxide yellow, 5C7 |
| ISP 3 | good | colorless | abundant, light gray | none |
| ISP 4 | moderate | colorless | scant, hygroscopic | none |
| ISP 5 | poor | colorless | brownish gray, 6F2 | none |
| ISP 6 | poor | colorless | none | none |
| ISP 7 | poor | colorless | none | none |
| Glucose - Asparagine | moderate | cream | none | none |
| Czapek's Sucrose - Nitrate | scant | colorless | none | none |
| Nutrient | poor | yellowish white, 3A2 | none | none |
| Modified Bennett's | moderate | colorless | moderate, hygroscopic | none |
| Thin Potato Carrot | poor | | moderate gray and white | none |
| ATCC 5 | moderate | colorless | moderate, gray | none |
| ATCC 172 | moderate | colorless | moderate, white and gray, 2B1 | none |
| Potato-Dextrose | poor | colorless | fair; white and gray | none |
| Tomato Juice | good | grayish orange, 5B4 | none | none |
| Tryptic Soy | poor | yellowish white, 3A2 | none | none |
| Xanthine | scant | yellowish white, 3A2 | none | none |

Color names and numbers from A. Kornerup and J. H. Wanscher. Reinhold Color Atlas. Reinhold Publishing Corporation. Copenhagen, Denmark. 1961.

TABLE 2

| Physiological Characteristics of Strain C39280-450-9 | |
|---|---|
| Growth temperature | 10° C.–37° C. |
| pH tolerance | 5.5–9 |
| NaCl tolerance | 1%–8% |
| Gelatin liquefaction | + |
| Starch hydrolysis | + |
| Urease | + |
| Milk coagulation peptonization | − + |
| Nitrate reduction | − |
| Lysozyme | − |

The morphological characteristics and cell chemistry of strain C39280-450-9 classify it as a *Streptomyces* species. Further classification as a *Streptomyces hygroscopicus* species is corroborated by the clustering of the organism's spiral spore chains and subsequent hygroscopic properties.

It is to be understood that the present invention is not limited to use of the particular preferred strains ATCC 53730 or ATCC 55006 or to organisms fully answering its description. It is especially intended to include other BMY-41950-producing strains or mutants of the described organisms which can be produced by conventional means such as x-radiation, ultraviolet radiation, treatment with nitrogen mustards, phage exposure and the like.

ANTIBIOTIC PRODUCTION

BMY-41950 may be produced by cultivating a BMY-41950-producing strain of *Streptomyces staurosporeus*, preferably *Streptomyces staurosporeus* ATCC 55006 or a mutant or variant thereof, or a BMY-41950-producing strain of *Streptomyces hygroscopicus*, preferably *Streptomyces hygroscopicus* strain C39280-450-9 (ATCC 53730) or a variant or mutant thereof, under submerged aerobic conditions in an aqueous nutrient medium. The organism is grown in a nutrient medium containing an assimilable carbon source for example sucrose, lactose, glucose, rhamnose, fructose, mannose, melibiose, glycerol or soluble starch. The nutrient medium should also contain an assimilable nitrogen source such as fish meal, peptone, soybean flour, peanut meal, cottonseed meal, corn steep liquor, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired, or they may be supplied as impurities of other constituents of the media.

Production of BMY-41950 can be affected at any temperature conducive to satisfactory growth of the producing organism, e.g. 20° to 40° C., but it is preferable to conduct the fermentation at 25°-35° C. most preferably 27°-32° C. A neutral pH is preferably employed in the medium and production of the antibiotic is carried out generally for a period of about seven to twelve days.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of BMY-41950. The medium in which the vegetative inoculum is produced can be the same as, or different from, that utilized in the tank as long as it is such that a good growth of the producing organism is obtained. Agitation during the fermentation can be provided by a mechanical impeller and conventional antifoam agents such as lard oil or silicon oil can be added if needed.

Isolation of the desired BMY-41950 antibiotic from the fermentation medium and purification of the BMY-41950 may be achieved by conventional solvent extraction and chromatographic techniques. A preferred isolation and purification procedure is illustrated in Example 2 below.

Subsequent to obtaining BMY-41950 by the fermentation procedure described above, it was found that BMY-41950 (7-oxostaurosporine) may also be chemically synthesized by oxidation of staurosporine. A representative oxidation is described below:

To 200 mg staurosporine in a 20 ml vial was added 5 ml anhydrous methylene chloride and a large excess (0.25 g) of manganese oxide (MnO$_2$-activated (Aldrich)). The mixture was sonicated at 23° C. for 20 minutes. Additional MnO$_2$ was added (0.25 g) with further sonication (20 minutes). This process was repeated four more times over two hours at which time the reaction mixture was allowed to stir overnight at 23° C. (14 additional hours). Dicalite was added to the reaction mixture which was then filtered, washed with acetone-methanol (9:1) and concentrated. The desired 7-oxostaurosporine was purified by vacuum liquid chromatography followed by reversed phase (C$_{18}$) HPLC to yield 5 mg of purified material.

PHYSICO-CHEMICAL PROPERTIES OF BMY-41950

The physico-chemical properties of BMY-41950 are as follows:

Description: yellow amorphous solid.
Molecular formula: $C_{28}H_{24}N_4O_4$.
Molecular weight: 480.
Mass spectrum: (M+H) ion 481 (Finnigan 4500 Single Quadrapole Mass Spectrometer).
Ultraviolet spectrum: Hewlett-Packard (HP) 8452A Diode Array Spectrophotometer. (concentration 0.2 mg/20 ml methanol).
Neutral: 420 nm (65),
372 nm(81), 337 nm sh,
318 nm(807), 308 nm sh,
288 nm (447), 260 nm (374),
240 nm (671),
360 MHz $^1$H-NMR: Bruker Model AM-3000 spectrometer. Dual carbon-proton probe. 5mm. Solvent: d$_6$-DMSO. Observed chemical shifts (ppm): 11.01 (s, 1H), 9.19 (d, 1H) 9.06 (d, 1H), 8.01 (d, 1H), 7.70 (d, 1H), 7.56 (m, 1H), 7.47 (m, 1H), 7.39 (m, 1H), 7.31 (m, 1H), 6.74 (m, 1H), 4.10 (m, 1H), 3.22 (s, 3H), 2.32 (s, 3H), 1.96 (m, 1H), 1.75 (m, 1H), 1.40 (s, 3H),
Solubility: soluble in dimethylsulfoxide (DMSO), tetrahydrofuran (THF), CHCl$_3$—CH$_3$OH (2:1 v/v).
Color reactions: Purple positive to iodoplatinic acid.
R$_f$ values: Silica gel 60 TLC (Merck).
CHCl$_3$—CH$_3$OH (9:1 v/v): 0.42. THF: 0.20.
Whatman MKC$_{18}$;
0.1 M NH$_4$OAc-THF (1:1 v/v): 0.25.

Based on the characterizing properties of BMY-41950, the antibiotic has been determined to be 7-oxostaurosporine, a new compound having the structural formula

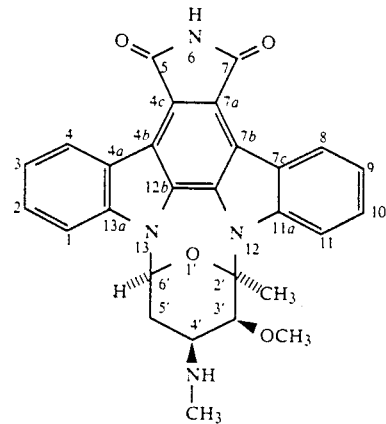

BIOLOGICAL ACTIVITY

BMY-41950 has been found to exhibit antimicrobial activity in standard in vitro screening tests. For example, BMY-41950 exhibits an MIC (Minimum Inhibitory Concentration) of 6.25 μg/ml vs. *Staphylococcus aureus* A9537 and 12.5 μg/ml vs. *Enterococcus faecalis* A20688.

BMY-41950 also exhibits antitumor activity when tested in conventional in vitro systems and in in vivo experimental animal tumor systems.

A more detailed disclosure of the antitumor testing of BMY-41950 is provided below.

BMY-41950 was tested for in vitro cytotoxic activity against a murine and a human tumor cell line. In vivo it was tested for activity against a murine leukemia tumor model. In vitro, mitomycin C and cisplatin were used as the reference compounds, while etoposide (VP-16) was used as the in vivo reference.

B16-F10 (murine melanoma) and HCT-116 (human colon cancer cell clone) cells were cultured in Complete McCoys Media. The media consists of 420 ml McCoys 5A media plus 500 mg sodium bicarbonate in 6 ml water, 6.56 mg L-serine, 1.5 mg L-asparagine and 82.4 mg sodium pyruvate in 2 ml water, 6.25 ml essential amino acids (50X, Gibco), 3.0 ml non-essential amino acids (100X, Gibco), 3 ml L-glutamine (200MM), 3 ml MEM vitamins (Gibco), 6.25 ml penicillin/streptomycin (Gibco) and 50 ml of heat-inactivated defined fetal calf serum.

The two cell lines are harvested during logarithmic phase cell growth and 3600 cells in 150 microliter media were placed in each well of a 96 well microtiter plate. After 24 hours incubation at 37 degrees Celsius in a 95% air/5% carbon dioxide humidified incubator to allow the cells to attach to the plate, fifty microliters of sample/reference drug is added to 11 of 12 of the top row of wells while 50 microliters of media is added to the 12th. The drugs/media are serially diluted (4 fold dilutions) down the 8 wells of the plate. The cells in the presence of drug/media are then incubated for 72 hours. After fixing with 10% formalin, cells killed by the drug were washed off the plate while those surviving cells are stained with 0.0075% crystal violet. After drying, the stain is solubilized with 10% ethanol and 1% acetic acid, the developed plate quantitated on a Dynatech MR 600 plate reader and the $IC_{50}$ values (drug concentration at which 50% cell death or growth inhibition occurs) calculated. The table below shows the data determined for BMY-41950 and the standard drugs mitomycin C and cisplatin.

| In Vitro Antitumor Activity ($IC_{50}$ in μg/ml or dilution) | | |
| --- | --- | --- |
| Drug | B16-F10 | HCT-116 |
| BMY-41950 | 0.98 μg/ml | 0.24 μg/ml |
| Cisplatin | 3.9 μg/ml | 15.6 μg/ml |
| Mitomycin C | 0.98 μg/ml | 0.98 μg/ml |

In vivo activity of BMY-41950 was determined in a murine leukemia tumor system. Female $CDF_1$ mice were intraperitoneally inoculated with 0.5 ml of diluted ascitic fluid containing $10^6$ lymphocytic leukemia P388 cells. Ten mice were untreated and the median survival time of this group was 10 days. Three groups of 4 mice each were treated with BMY-41950 on days 1, 2, 3, 4 and 5 post tumor implant. The drug was administered ip after being initially dissolved in DMSO, Tween 80 and buffered saline. Groups treated with 18 and 6 mg/kg/day suffered drug-induced toxicity and all mice died prior to day 7. The third group, receiving 2 mg/kg/day, had a median survival time of 13 days. Thus the % T/C (survival time of drug treated/survival time of untreated controls × 100) was 130%. The criteria for antitumor activity in this murine tumor test is a % T/C of 125 or greater. Thus. BMY-41950 fulfilled the criteria for antitumor activity in the P388 murine leukemia antitumor model.

THERAPEUTIC USE

As mentioned above, BMY-41950 exhibits antimicrobial activity, e.g. activity against bacteria such as *Staphylococcus aureus* and *Enterococcus faecalis*.

The present invention, therefore, provides a method for treating microbial infections susceptible to BMY-41950, which comprises administering to a host, e.g. a warmblooded mammal, in need of such treatment BMY-41950 or a pharmaceutical composition thereof in an amount sufficient to treat such infections.

BMY-41950 also exhibits antitumor activity against mammalian malignant tumors.

In another aspect the present invention provides a method of treating a mammalian host affected by a malignant tumor sensitive to BMY-41950, which comprises administering to said host a tumor-inhibiting dose of BMY-41950 or a pharmaceutical composition thereof.

In yet another aspect, the present invention provides pharmaceutical compositions comprising an effective antimicrobial or tumor-inhibiting amount of BMY-41950 in combination with an inert pharmaceutically acceptable carrier or diluent. Such compositions may contain other antimicrobial or antitumor agents and may be made up in any form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antimicrobial agent the BMY-41950 or pharmaceutical composition thereof is administered so that the concentration of active ingredient is greater than the minimum inhibitory concentration for the particular organism being treated.

For use as an antitumor agent. BMY-41950 or a pharmaceutical composition thereof may be administered in substantially the same manner as compound UCN-01 described in EP 238,011. Optimal dosages and regimens of BMY-41950 for a given mammalian host can be readily ascertained by those skilled in the art. It will of course be appreciated that the actual dose of BMY-41950 used will vary according to the particular composition formulated, the mode of application and the particular situs, host and disease being treated. Many factors that modify the action of the drug will be taken into account including age, sex, weight, diet, time of administration, route of administration, rate of excretion, condition of the patient, drug combinations, reaction sensitivities and severity of the disease.

The following examples are provided for illustrative purposes only and are not intended to limit the scope of the invention. Nutrisoy is soy flour marketed by Archers Daniels Midland Co., Decatur, Ill. Pharmamedia is cottonseed endosperm flour marketed by Buckeye Oil Seed Products Co., Fort Worth, Tex. S. J. Starch (Staclipse J-UB starch) is corn starch marketed by A. E. Staley Manufacturing Co., Decatur, Ill.

EXAMPLE 1

Fermentation of BMY-41950

*Streptomyces staurosporeus* strain R10069 (ATCC 55006) was maintained and transferred in test tubes on agar slants of yeast extract-malt extract agar supplemented with $CaCO_3$. This medium consists of 4.0 g of dextrose, 4.0 g of yeast extract, 10 g malt extract, 1.5 g calcium carbonate and 20 g agar made up to one liter with distilled water. With each transfer the agar slant was incubated for 5 to 7 days at 28° C. To prepare an inoculum for the production phase, the surface growth from the slant culture was transferred to a 500 ml Erlenmeyer flask containing 100 ml of sterile medium consisting of 30 g of cerelose, 10 g of Pharmamedia (cottonseed endosperm flour), 10 g of Nutrisoy (soy flour) and 3.0 g of calcium carbonate made up in one liter of distilled water. This vegetative culture was incubated at 28° C. for 48 hours on a rotary shaker set at 250 rev/min. Five mls of this vegetative culture were inoculated into 500 ml Erlenmeyer flasks each containing 100 ml of production medium consisting of 60 g of S. J. Starch (corn starch), 10 g of cerelose, 10 g of Nutrisoy, 5 g of Debittered Brewer's yeast, 1 g of ferrous sulfate heptahydrate, 1 g of ammonium sulfate, 1 g ammonium phosphate monobasic and 10 g of calcium carbonate made up to one liter with distilled water. The production culture was incubated at 28° C. on a rotary shaker and the agitation rate was set at 250 rev/min. Optimal production occurred generally at 216 to 264 hours.

EXAMPLE 2

Isolation and Purification of BMY-41950

General Methods: Solvents

Solvents were not redistilled before use. Methanol, ethyl acetate, chloroform, acetone and ethyl ether were ACS reagent grade. Water refers to in-house deionized water passed through a Barnstead Nanopure II system. Tetrahydrofuran was B & J Brand HPLC grade solvent. Ammonium acetate was Fisher HPLC grade.

Broth Filtration

Whole fermentation broth was filtered through a 12" Tolhurst Laboratory Centerslung Centrifugal Filter Unit (Model IB15, Ametek, Inc.) lined with a sewn filter bag containing Dicalite (speedplus) filter aid.

Thin later chromatography (TLC)

Normal phase TLC was carried out on silica gel 60 F-254 plates (EM reagents, Cat. 5765, 5 cm×10 cm×0.25 mm thick). Reversed phase TLC was accomplished with Whatman $MKC_{18}$ plates (Cat. 4803-110, 0.2 mm thick). Plates were developed in Whatman cylindrical jars with caps and 10 ml of eluant. Developed, air-dried plates were visualized with 254 and 266 nm ultraviolet light. Normal phase TLC plates were also visualized with iodoplatinic acid spray reagent for alkaloids.

Vacuum Liquid Chromatography (VLC)

A VLC apparatus consists of a Buchner funnel (Kontes, Art. K-954100) containing a sealed-in glass disc (M porosity, 10-15 $\mu$), a side hose connection for vacuum and a lower 24/40 joint for attachment of receiving flasks.

The funnel is dry filled with adsorbent and a sufficient volume of the least polar eluting solvent is pulled through under vacuum to form a tightly packed 5 cm adsorbent bed height.

Sample can be pre-adsorbed and applied to the prepared funnel or is applied in a solution of the least polar eluting solvent.

An isocratic elution can be carried out where predetermined volumes constitute the fractions, or the eluant volumes are increased in polarity resulting in a step gradient. The funnel is sucked dry after each volume of eluting solvent.

Semi-preparative HPLC

The following components were used to construct an HPLC system: Waters Associates Model 590 Solvent Delivery System pump; Knaver Model 87 variable wavelength detector set at 320 nm; Waters Associates Model U6K injector; Heath Model SR-204 strip chart recorder: Whatman Partisil 16 ODS-3 column (10 mm×50 cm). Components were connected with 316 stainless steel tubing (1.6 mm o.d.-0.23 mm i.d.). Eluant was pumped at 4 ml/min.

Isolation

Extraction

Whole broth (10 l) was centrifugally filtered using 800 g of Dicalite filter aid. The mycelial mat was suspended in tetrahydrofuran (8 l) for 3 hours, filtered through a 24 cm Buchner funnel (Coors No. 11) and the solids rinsed with an additional 2 liter volume of acetone. The combined organic volume was evaporated under reduced pressure to yield 33 g of residue.

The filtrate was extracted once with a mixture of THF (3 l) and ethyl ether (6 l) in a separatory funnel. The organic layer yielded 400 mg of residue upon solvent removal under reduced pressure. A second extraction of the filtrate with ethyl acetate (2 l), gave 266 mg of residue upon concentration.

The three crude residues from the extraction process were combined for further purification.

Acid-Base Extraction

The crude solids (33.76 g) were dissolved in 250 ml of 0.5 M HCl (pH 1.5). The acidic aqueous layer was extracted with three 150 ml volumes of chloroform in a separatory funnel. The combined organic layers yielded 4.04 g of residue upon concentration in vacuo.

The aqueous layer was adjusted to pH 9.5-10 with aqueous ammonia. Three additional washes with 150 ml volumes of chloroform gave 1.11 g of residue after concentration of the combined organic layers.

First VLC—Step Gradient

A 30 ml Kontes sintered glass funnel was packed with 16 g of Lichroprep Si 60, 15-25 $\mu$ (EM Science, Art. 9336) in the usual manner. The chloroform extract at basic pH (1.11 g) was preadsorbed onto an additional 3 g of adsorbant and applied to the funnel as a chloroform slurry. Nine fractions were generated from the volumes and composition of eluant shown below:

| Fraction Number | eluant volume | eluant composition | residue weight |
| --- | --- | --- | --- |
| 1 | 100 ml | $CHCl_3$ | 171 mg |
| 2 | 100 ml | $CHCl_3$ | 32 mg |
| 3 | 100 ml | $CHCl_3$-1% MeOH | 13 mg |
| 4 | 100 ml | $CHCl_3$-1% MeOH | 54 mg |
| 5 | 100 ml | $CHCl_3$-2% MeOH | 208 mg |

| Fraction Number | eluant volume | eluant composition | residue weight |
| --- | --- | --- | --- |
| 6 | 100 ml | CHCL$_3$-2% MeOH | 43 mg |
| 7 | 100 ml | CHCl$_3$-2% MeOH | 24 mg |
| 8 | 200 ml | CHCl$_3$-5% MeOH | 109 mg |
| 9 | 200 ml | CHCl$_3$-50% MeOH | 289 mg |

TLC analysis showed that fractions 3 and 4 contained the yellow fluorescing material characteristic of BMY-41950 so they were combined.

Second VLC

A 15 ml Kontes sintered glass funnel was packed with 7.5 g of Lichroprep Si 60, 15-25 μ (EM Science, Art. 9336). Fractions containing the yellow fluorescer (67 mg) were dissolved in 5 ml ethyl acetate and applied to the top of the funnel. The desired yellow band was visibly observed eluting and the fractions cut accordingly as follows:

| Fraction Number | eluant volume | eluant composition | residue weight |
| --- | --- | --- | --- |
| 1 | 100 ml | EtOAc | 39 mg |
| 2 | 75 ml | EtOAc | 20 mg |
| 3 | 100 ml | EtOAc | 19 mg |
| 4 | 100 ml | THF-10% MeOH | 15 mg |

The second fraction was shown to possess the yellow fluorescer by TLC.

HPLC Purification

The advanced fraction containing BMY-41950 (20 mg) was dissolved in 0.3 ml THF and injected onto a Whatman Partisil 10 ODS-3 column (50 cm × 10 mm) equilibrated with 0.2 M NH$_4$OAc - THF (1:1) flow rate 4 ml/min. After two blue fluorescing materials eluted in 8.7 and 13 minutes, BMY-41950 eluted in 17 minutes over two fractions. These fractions were pooled and extracted with two 25 ml volumes of chloroform. The combined chloroform layers were concentrated to dryness in vacuo to yield BMY-41950 (1.8 mg).

We claim:

1. A process for producing BMY-41950 having the formula

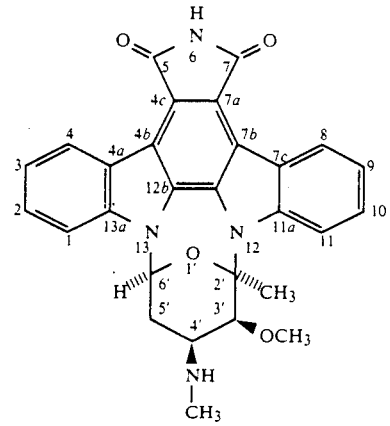

which comprises cultivating *Streptomyces staurosporeus* ATCC-55006 or a BMY-41950-producing mutant or variant thereof in an aqueous nutrient medium containing assimilable sources or carbon and nitrogen under submerged aerobic conditions until a substantial amount of BMY-41950 is produced by said organism in said culture medium and recovering the BMY-41950 from the culture medium.

2. A process of producing BMY-41950 having the formula

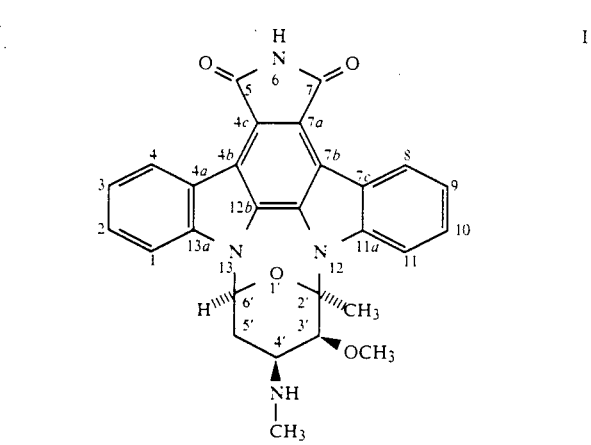

which comprises cultivating *Streptomyces hygroscopicus* stain C39280-450-9 (ATCC 53730 or a BMY-41950-producing mutant or variant thereof in an aqueous nutrient medium containing assimilable sources of carbon and nitrogen under submerged aerobic conditions until a substantial amount of BMY-41950 is produced by said organism in said culture medium and recovering the VMY-41950 from the culture medium.

3. A biologically pure culture of *Streptomyces hygroscopicus* strain C39280-450-9 (ATCC 53730), said culture being capable of producing the antibiotic BMY-41950 in a recoverable quantity upon cultivation in an aqueous nutrient medium containing assimilable sources of carbon and nitrogen.

* * * * *